United States Patent [19]

De La Mettrie et al.

[11] Patent Number: 5,725,847
[45] Date of Patent: Mar. 10, 1998

[54] SOLID HAIR-REMOVING COMPOSITION CONTAINING A PARTICULAR STRUCTURING AGENT

[75] Inventors: Roland De La Mettrie, Le Vesinet; Arnaud De Labbey, Aulnay-Sous-Bois; Lylan N'Guyen, L'Hay Les Roses, all of France

[73] Assignee: L'Oreal, Paris, France

[21] Appl. No.: 500,749

[22] Filed: Jul. 11, 1995

[30] Foreign Application Priority Data

Jul. 11, 1994 [FR] France .................. 94-08564

[51] Int. Cl.$^6$ .................................. A61K 7/155
[52] U.S. Cl. .................. 424/70.1; 424/70.5; 424/73; 514/951
[58] Field of Search ............ 424/73, 70.1, 70.5

[56] References Cited

U.S. PATENT DOCUMENTS

| | | | |
|---|---|---|---|
| 3,903,410 | 9/1975 | Akrongold et al. | 252/91 |
| 4,734,099 | 3/1988 | Cyprien | 8/160 |

FOREIGN PATENT DOCUMENTS

| | | |
|---|---|---|
| WO-A-8900041 | 1/1989 | WIPO |
| WO-A-9414402 | 7/1994 | WIPO |

OTHER PUBLICATIONS

Database WPI, Week 8246, Derwent Publications Ltd., London, GB; AN 82-98267E & JP-A-57 163 308 (Shinmeiwa Ind KK) 7 Oct. 1982.

Primary Examiner—James M. Spear
Attorney, Agent, or Firm—Oblon, Spivak, McClelland, Maier & Neustadt, P.C.

[57] ABSTRACT

The invention relates to a hair-removing composition containing, in a cosmetically acceptable medium, a structuring agent insoluble in this medium and formed of solid particles, which imparts a deformable solid appearance to the composition in which the medium is contained, this agent being capable of being removed from the skin using a diluent. These particles are, in particular, expanded copolymer particles of acrylonitrile and an acrylic and/or styrene and/or vinylidene chloride monomer.

34 Claims, No Drawings

SOLID HAIR-REMOVING COMPOSITION CONTAINING A PARTICULAR STRUCTURING AGENT

BACKGROUND OF THE INVENTION

1. Field of the Invention

The present invention relates to a novel hair-removing composition of deformable solid appearance. On account of its extreme softness, this composition may be applied either to the face or to the body, and especially around the lips, on the arms, on the legs and under the armpits.

The invention also relates to a cosmetic treatment process for the removal of unwanted hair.

The invention further relates to the use of a specific structuring agent in a hair-removing composition.

2. Discussion of the Background

Apart from mechanical means for hair removal such as razors, the methods of hair removal currently used consist in applying hair-removing compositions, such as hair-removing creams or waxes, to the parts from which the hair is to be removed.

The waxes are applied, usually after they have been melted, and they are then removed after leaving in place for a certain amount of time, which thereby involves the stripping out of the hairs. Hair removal using wax is difficult when hot wax has to be handled, and it is also painful since the hairs are stripped out violently when the hardened wax is removed. Furthermore, the hair removal obtained is not always satisfactory.

In a simplified manner, a hair-removing cream comprises a hair-softening agent, usually a thiol, in a cosmetically acceptable support or medium of high pH, for example of the order of 12 or 12.5. The hair-removing cream is applied cold and causes the hairs to fall out by softening them. Hair-removing cream are difficult to measure out on account of their fluidity and often give incomplete hair removal. Furthermore, after each hair removal treatment of the skin, it is necessary to remove the hair-removing cream and to rinse the area of skin from which the hair has been removed and, unfortunately, many hair-removing creams have the drawback of being difficult to remove and/or of leaving traces of products on the skin.

In addition, regardless of the hair removal technique chosen, it is usually irritant to the skin.

Moreover, users are increasingly seeking novel product textures and new product concepts.

The subject of the present invention is, indeed, a novel hair-removing composition which makes it possible in particular to overcome the drawbacks mentioned above. In particular, this composition is rinsed off in a noteworthy manner and has a quite uncommon texture. In addition, it is simple to apply.

The Applicant has found, surprisingly, that it was possible to impart a deformable solid appearance to a hair-removing composition by using an original structuring or texturing agent.

SUMMARY OF THE INVENTION

Thus, the invention relates to a hair-removing composition, comprising, in a cosmetically acceptable medium, i) a hair-removing agent; and ii) a structuring agent insoluble in said medium and formed of solid particles, which imparts a deformable solid appearance to said hair-removing composition in which said medium is contained, said structuring agent being capable of being removed from skin using a diluent.

Another subject of the invention is the use of a structuring agent in a hair-removing composition in order to impart a deformable solid appearance thereto, this agent being formed of solid particles and being capable of being removed using a diluent.

One of the advantages of this solid texture is that there is no risk of the composition of the invention escaping from its packaging, especially during transport. Moreover, this composition is very easy to handle and does not run between the fingers. It is much easier to measure out than the usual creams.

DETAILED DESCRIPTION OF THE PREFERRED EMBODIMENTS

According to the invention, the composition is of a dry, deformable solid appearance, does not stain and resembles marshmallow (see document U.S. Pat. No. 3,682,659 for the consistency of marshmallow). This solid may be modelled like children's plasticine. It may be broken readily by hand so as to take only the required amount of product. In particular, this composition may be packaged in single-dose form and, for example, in the form of small cubes or beads or in pyramid-shaped packaging form.

By virtue of the particles of the invention, it is possible in particular to obtain a homogeneous (deformable solid) structure for constituents which normally lead to two separate phases (immiscible constituents, for example oil/water).

For the purpose of obtaining a solid which feels soft and pleasant, it is preferable to use particles having a particle size of from 1 µm to 300 µm, preferably from 5 µm to 200 µm and more preferably from 10 µm to 100 µm and most preferably from 15 µm to 40 µm.

The great softness provided by these particles allows the hair-removing composition of the invention to be used by individuals with sensitive skin.

In order to impart a light and airy appearance to the composition of the invention, particles having a density of less than 0.09 kg/cm$^3$ and better still of less than 0.06 kg/cm$^3$ and even better still of less than 0.04 kg/cm$^3$ are advantageously used.

For the purpose of obtaining this low density, hollow particles filled with a gas are advantageously used. Specific non-limiting examples of such a gas includes air, nitrogen, isobutane, isopentane, carbon dioxide, chlorfluorcarbons or hydrochlorofluorocarbons etc.

According to another advantageous characteristic of the invention, the particles are in the form of beads. It is, however, possible to use particles in the form of fibers.

These particles may be made of various inert materials which do not react chemically with the cosmetically acceptable medium or support; in particular, these particles do not react with the oils, the surfactants, the water and the various other constituents of the composition, such as the active agents.

The structuring agent of the invention has the particular feature of being readily removed from the skin by simple dilution. It acts, in fact, as a vehicle or reservoir for the cosmetic support. It moreover enables the support and especially the active agent or agents, contained in the deformable solid, to be recovered, when necessary, by simple dilution with water. This is probably due to the fact that the cosmetic support is housed in the interparticulate spaces of the solid and not in the particles.

Besides water, water to which one or more polar solvents such as lower $C_{1-5}$ alcohols (ethanol or isopropanol) and glycols (propylene glycol), and to which one or more surfactants has been added, may be used as diluent. Salt-charged water may also be used.

As a selection criterion for the structuring agent, the following test may be performed:
- addition of determined particles in water containing a dye conventionally used in the field of hair removal, such as azulene, until a colored paste is obtained,
- pouring of a drop of water onto the paste.

When the paste is much clearer at the point of impact of the drop of water than the rest of the paste, this means that the particles in question are candidates for structuring agent. On the other hand, when the paste is not decolorized at the point of impact, the particles in question are not at all suitable.

The inert particles are advantageously made of glass or of thermoplastic materials, for instance polyamides such as nylon, polymers or copolymers of acrylonitrile, of vinylidene chloride, of vinyl chloride and/or of acrylic or styrene monomer, which may be expanded. The acrylic monomer is, for example, a methyl or ethyl acrylate or methacrylate. The styrene monomer is, for example, α-methylstyrene or styrene.

As glass particles which may be used in the invention, there may be mentioned the hollow glass beads sold by the company 3M under the reference SCOTCHLITE GLASS BUBBLES S 22. 95% of these beads have a diameter of less than 74 µm.

Nylon particles which may be used are the "ORGASOL" particles sold by the company Atochem. These particles are porous solid spheres of diameter ranging from 5 µm to 60 µm.

The particles are preferably hollow deformable particles of an expanded copolymer of vinylidene chloride and acrylonitrile or of vinylidene chloride, acrylonitrile and methacrylate. It is possible, for example, to use a copolymer containing: from 0% to 60% of units derived from vinylidene chloride, from 20% to 90% of units derived from acrylonitrile and from 0% to 50% of units derived from an acrylic or styrene monomer, the sum of these percentages (by weight) being equal to 100. These particles are especially in the dry or hydrated state and may be obtained, for example, according to the processes described in the patents and patent applications EP-A-56,219, EP-A-348,572, EP-A-320,473, EP-A-112,807 and U.S. Pat. No. 3,615,972.

These hollow particles may, for example, be those formed of a terpolymer of acrylonitrile, methacrylate and vinylidene chloride and sold under the trade name EXPANCEL by the company Nobel Caaco, and in particular under the references 551 DE 12 (particle size of approximately 12 µm and density of 40 kg/m³), 551 DE 20 (particle size of approximately 30 µm and density of 65 kg/m³) and 551 DE 50 (particle size of approximately 40 µm).

It is also possible to use particles formed of the same terpolymer and having a particle size of approximately 18 µm and a density of approximately 60 to 80 kg/m³, referred to here as EL 23, or having a particle size of approximately 34 µm and a density of approximately 20 kg/m³, referred to here an EL 43, or having a particle size of approximately 150 µm, referred to here an EL 55.

As other hollow polymer particles which may be used in the invention, there may also be mentioned the polymers and the copolymers obtained from itaconic, citraconic, maleic and/or fumaric acid and from vinyl acetate or lactate esters (see in this regard document JP-A-2-112,304), or alternatively non-expanded copolymer particles of vinylidene chloride and acrylonitrile or of vinylidene chloride, acrylonitrile and methacrylate, sold under the trade name EXPANCEL, with the reference 551 WU.

In contrast, particles of corn starch, pyrogenous silica or of non-expanded polyester, polyurethane or polyethylene do not make it possible to obtain a solid composition which is removed well from the skin during rinsing.

It is, admittedly, known to modify the viscosity of a liquid medium with solid particles (see on this subject the article Elsevier Sequoia, 1992, Progress in Organic Coatings, 21, p. 255–267, from A. Toussaint "Choice of Rheological model for steady flow: application to industrial concentrated suspensions") but nobody to date has either described or suggested the use of the solid product, obtained from a certain concentration of particles, in the field of hair removal in order to store the medium in which the particles are dispersed.

In other words, the production or otherwise of the deformable solid is linked to the amount of structuring agent used in the composition; above a certain quantity of particles, referred to as the critical pigment charge volume and abbreviated to CPCV, a sudden increase in the viscosity of the medium is observed. The CPCV is a function of the medium and of the nature of the particles; it must thus be determined every time. Its determination poses no problem to those skilled in the art. It is possible, for example, to use the official ASTM method in order to determine the CPCV. Preferably, the amount of particles is equal to or greater than the CPCV.

Another subject of the invention in the use of the composition defined above for hair removal.

Thus, another subject of the invention is a process for removing hair from the skin, consisting in applying a composition as defined above to the skin, and then in rinsing the skin.

The composition of the invention may contain, in addition to the structuring particles, all the constituents conventionally used in hair-removing compositions. These constituents are, in particular, hair-softening agents such as thiols and especially calcium thioglycolate, mineral, vegetable, synthetic or silicone-containing oils, water, alcoholic solvents, screening agents, fragrances, surfactants, polymers, preserving agents, antioxidants, pH regulators, sequestering agents, fillers, etc.

Having generally described this invention, a further understanding can be obtained by reference to certain specific examples which are provided herein for purposes of illustration only and are not intended to be limiting unless otherwise specified.

EXAMPLE

Hair-Removing Paste

| | |
|---|---|
| Calcium thioglycolate | 8% |
| Cetylstearyl alcohol/oxyethylenated cetylstearyl alcohol (33 EO) (90/20 mixture sold under the name CIRE LANOL CTO by the company Seppic) (emulsifying agent) | 4% |
| Anhydrous calcium oxide (filler) | 3% |
| EXPANCEL 551 DE 20 | 3% |
| Water | qs 100% |

A smooth white paste which feels soft, is easily modellable and is easy to apply and to remove is obtained.

The particles have the advantage, moreover, of strongly absorbing the odor of the thiols, which imparts a much fainter odor to the composition than that of the hair-removing compositions of the prior art.

This preparation is applied, especially by hand, to the area from which hair is to be removed. It is left to act for 10 minutes, and then rinsed off thoroughly with water. Very good hair removal in observed, with no problems of irritation.

Obviously, numerous modifications and variations of the present invention are possible in light of the above teachings. It is therefore to be understood that within the scope of the appended claims, the invention may be practiced otherwise than as specifically described herein.

This application is based on French patent application FR 94-08564, filed in the French Patent Office on Jul. 11, 1994, the entire contents of which are hereby incorporated by reference.

What is claimed as new and desired to be secured by Letters Patent of the United States is:

1. A hair-removing composition, comprising:
   i) a deformable solid appearance;
   ii) hair-removing effective amount of a hair-softening agent contained in a cosmetically acceptable medium, said hair-softening agent being a thiol; and
   iii) particles, insoluble in said medium, having a particle diameter ranging from 1 to 300 µm, in a concentration at least equal to a critical pigment charge volume with respect to said composition; wherein
   said particles are hollow or expanded thermoplastic resin particles or hollow glass particles, said hollow or expanded thermoplastic resin particles comprising a polymer selected from the group consisting of:
      polyamides, acrylonitriles, vinylidene chlorides, vinyl chlorides, expanded acrylics, expanded styrenes, ethyl acrylate, ethyl methacrylate, methyl acrylate, methyl methacrylate, expanded copolymers of vinylidene chloride and acrylonitrile, expanded terpolymers of vinylidene chloride, acrylonitrile and methacrylate, itaconic acid-containing copolymers, citraconic acid-containing copolymers, maleic acid-containing copolymers, fumaric acid-containing copolymers, vinyl acetate, vinyl lactate, vinyl acetate esters, vinyl lactate esters, and porous nylon, and a mixture thereof.

2. A hair-removing composition, comprising:
   i) a deformable solid appearance;
   ii) a hair-removing effective amount of a hair-softening agent contained in a cosmetically acceptable medium; and
   iii) particles, insoluble in said medium, having a particle diameter ranging from 1 to 300 µm, in a concentration at least equal to a critical pigment charge volume with respect to said composition; wherein
   said particles are hollow or expanded thermoplastic resin particles or hollow glass particles, said hollow or expanded thermoplastic resin particles comprising a polymer selected from the group consisting of:
      polyamides, acrylonitriles, vinylidene chlorides, vinyl chlorides, expanded acrylics, expanded styrenes, ethyl acrylate, ethyl methacrylate, methyl acrylate, methyl methacrylate, expanded copolymers of vinylidene chloride and acrylonitrile, expanded terpolymers of vinylidene chloride, acrylonitrile and methacrylate, itaconic acid-containing copolymers, citraconic acid-containing copolymers, maleic acid-containing copolymers, fumaric acid-containing copolymers, vinyl acetate, vinyl lactate, vinyl acetate esters, vinyl lactate esters, and porous nylon, and a mixture thereof.

3. The composition of claim 2, wherein said particles have a particle size of from 10 µm to 100 µm.

4. The composition of claim 2, wherein said particles have a density of less than 0.09 kg/cm$^3$.

5. The composition of claim 2, wherein said particles have a density of less than 0.04 kg/cm$^3$.

6. A process for removing hair from the skin, comprising:
   i) applying a hair-removing composition to skin;
   ii) allowing said composition to act; and
   iii) rinsing said skin; wherein
   said hair-removing composition comprises:
      i) a deformable solid appearance;
      ii) a hair-removing effective amount of a hair-softening agent contained in a cosmetically acceptable medium; and
      iii) particles, insoluble in said medium, having a particle diameter ranging from 1 to 300 µm, in a concentration at least equal to a critical pigment charge volume with respect to said composition; wherein
   said particles are hollow or expanded thermoplastic resin particles or hollow glass particles, said hollow or expanded thermoplastic resin particles comprising a polymer selected from the group consisting of:
      polyamides, acrylonitriles, vinylidene chlorides, vinyl chlorides, expanded acrylics, expanded styrenes, ethyl acrylate, ethyl methacrylate, methyl acrylate, methyl methacrylate, expanded copolymers of vinylidene chloride and acrylonitrile, expanded terpolymers of vinylidene chloride, acrylonitrile and methacrylate, itaconic acid-containing copolymers, citraconic acid-containing copolymers, maleic acid-containing copolymers, fumaric acid-containing copolymers, vinyl acetate, vinyl lactate, vinyl acetate esters, vinyl lactate esters, and porous nylon, and a mixture thereof.

7. A method of imparting a deformable solid appearance to a hair-removing composition comprising:
   adding to a hair-softening agent in a cosmetically acceptable medium,
   particles having a diameter ranging from 1 to 300 µm, to a concentration at least equal to a critical pigment charge volume with respect to said composition; wherein
   said particles are selected from the group consisting of hollow or expanded thermoplastic resin particles, hollow glass particles, and non-hollow, non-expanded thermoplastic resin particles; wherein
   said hollow or expanded thermoplastic resin particles comprise a polymer selected from the group consisting of:
      polyamides, acrylonitriles, vinylidene chlorides, vinyl chlorides, expanded acrylics, expanded styrenes, ethyl acrylate, ethyl methacrylate, methyl acrylate, methyl methacrylate, expanded copolymers of vinylidene chloride and acrylonitrile, expanded terpolymers of vinylidene chloride, acrylonitrile and methacrylate, itaconic acid-containing copolymers, citraconic acid-containing copolymers, maleic acid-containing copolymers, fumaric acid-containing copolymers, vinyl acetate, vinyl lactate, vinyl acetate esters, vinyl lactate esters, and porous nylon, and a mixture thereof; and wherein said non-hollow, non-expanded thermoplastic resin particles comprise a polymer selected from the group consisting of:

polyamide, polymers or copolymers of acrylonitrile, vinylidene chloride, vinyl chloride, polymers or copolymers of acrylic monomer, polymers or copolymers of styrene monomer, non-expanded copolymers of vinylidene chloride and acrylonitrile, non-expanded copolymers of vinylidene chloride, acrylonitrile and methacrylate, and mixtures thereof.

8. A hair-removing composition, comprising:

i) a deformable solid appearance;

ii) a hair-removing effective amount of a calcium thioglycolate contained in a cosmetically acceptable medium; and iii) particles, insoluble in said medium, having a particle diameter ranging from 1 to 300 μm, in a concentration at least equal to a critical pigment charge volume with respect to said composition; wherein said particles are hollow or expanded thermoplastic resin particles or hollow glass particles, said hollow or expanded thermoplastic resin particles comprising a polymer selected from the group consisting of polyamides, acrylonitriles, vinylidene chlorides, vinyl chlorides, expanded acrylics, expanded styrenes, ethyl acrylate, ethyl methacrylate, methyl acrylate, methyl methacrylate, expanded copolymers of vinylidene chloride and acrylonitrile, expanded terpolymers of vinylidene chloride, acrylonitrile and methacrylate, itaconic acid-containing copolymers, citraconic acid-containing copolymers, maleic acid-containing copolymers, fumaric acid-containing copolymers, vinyl acetate, vinyl lactate, vinyl acetate esters, vinyl lactate esters, and porous nylon, and a mixture thereof.

9. The method of claim 7, wherein said particles have a particle size ranging from 10 μm to 100 μm.

10. The method of claim 7, wherein said particles have a density of less than 0.09 kg/cm$^3$.

11. The method of claim 7, wherein said particles have a density of less than 0.04 kg/cm$^3$.

12. A hair-removing composition, comprising:

i) a deformable solid appearance;

ii) a hair-removing effective amount of a hair-softening agent contained in a cosmetically acceptable medium; and iii) particles, insoluble in said medium, having a particle diameter ranging from 1 to 300 μm, in a concentration at least equal to a critical pigment charge volume with respect to said composition; wherein said particles are non-hollow, non-expanded thermoplastic resin particles selected from the group consisting of polyamide, polymers or copolymers of acrylonitrile, vinylidene chloride, vinyl chloride, polymers or copolymers of acrylic monomer, polymers or copolymers of styrene monomer, non-expanded copolymers of vinylidene chloride and acrylonitrile, non-expanded copolymers of vinylidene chloride, acrylonitrile and methacrylate, and mixtures thereof.

13. The composition of claim 12, wherein said particles have a particle size of from 10 μm to 100 μm.

14. The composition of claim 12, wherein said particles have a density of less than 0.09 kg/cm$^3$.

15. The composition of claim 14, wherein said particles have a density of less than 0.04 kg/cm$^3$.

16. The composition of claim 12, wherein said hair-softening agent is a thiol.

17. The composition of claim 16, wherein said thiol is calcium thioglycolate.

18. A process for removing hair from the skin, comprising:

i) applying a hair-removing composition to skin;

ii) allowing said composition to act; and iii) rinsing said skin; wherein said hair-removing composition comprises:

i) a deformable solid appearance;

ii) a hair-removing effective amount of a hair-softening agent contained in a cosmetically acceptable medium; and iii) particles, insoluble in said medium, having a particle diameter ranging from 1 to 300 μm, in a concentration at least equal to a critical pigment charge volume with respect to said composition; wherein said particles are non-hollow, non-expanded thermoplastic resin particles selected from the group consisting of polyamide, polymers or copolymers of acrylonitrile, vinylidine chloride, vinyl chloride, polymers or copolymers of acrylic monomer, polymers or copolymers of styrene monomer, non-expanded copolymers of vinylidene chloride and acrylonitrile, non-expanded copolymers of vinylidene chloride, acrylonitrile and methacrylate, and mixtures thereof.

19. The process of claim 18, wherein said particles have a particle size of from 10 μm to 100 μm.

20. The process of claim 18, wherein said particles have a density of less than 0.09 kg/cm$^3$.

21. The process of claim 20, wherein said particles have a density of less than 0.04 kg/cm$^3$.

22. The process of claim 18, wherein said hair-softening agent is a thiol.

23. The process of claim 22, wherein said thiol is calcium thioglycolate.

24. The composition of claim 1, wherein said particles have a particle size of from 10 μm to 100 μm.

25. The composition of claim 1, wherein said particles have a density of less than 0.09 kg/cm$^3$.

26. The composition of claim 25, wherein said particles have a density of less than 0.04 kg/cm$^3$.

27. The process of claim 6, wherein said particles have a particle size of from 10 μm to 100 μm.

28. The process of claim 6, wherein said particles have a density of less than 0.09 kg/cm$^3$.

29. The process of claim 28, wherein said particles have a density of less than 0.04 kg/cm$^3$.

30. The method of claim 7, wherein said hair-softening agent is a thiol.

31. The process of claim 30, wherein said thiol is calcium thioglycolate.

32. The composition of claim 8, wherein said particles have a particle size of from 10 μm to 100 μm.

33. The composition of claim 8, wherein said particles have a density of less than 0.09 kg/cm$^3$.

34. The composition of claim 33, wherein said particles have a density of less than 0.04 kg/cm$^3$.

* * * * *

UNITED STATES PATENT AND TRADEMARK OFFICE
CERTIFICATE OF CORRECTION

PATENT NO. : 5,725,847
DATED : March 10, 1998
INVENTOR(S) : Roland DE LA METTRIE et al.

It is certified that error appears in the above-identified patent and that said Letters Patent is hereby corrected as shown below:

Column 3, line 61, "here an" should read --here as--;

Column 3, line 62, "here an" should read --here as--;

Column 4, line 31, "invention in" should read --invention is--;

Column 5, line 6, "removal in" should read --removal is--.

Signed and Sealed this

Ninth Day of February, 1999

Attest:

Attesting Officer

*Acting Commissioner of Patents and Trademarks*